(12) United States Patent
Medoff

(10) Patent No.: US 7,267,678 B2
(45) Date of Patent: Sep. 11, 2007

(54) INTRAMEDULLARY IMPLANT FOR FRACTURE FIXATION

(75) Inventor: Robert J. Medoff, 30 Aulike St., Suite 506, Kailua, HI (US) 96734

(73) Assignees: Robert J. Medoff, Kailua, HI (US); Lars G. Tellman, Falsterbo (SE); David Medoff, Valencia, CA (US)

( * ) Notice: Subject to any disclaimer, the term of this patent is extended or adjusted under 35 U.S.C. 154(b) by 433 days.

(21) Appl. No.: 10/675,864

(22) Filed: Sep. 30, 2003

(65) Prior Publication Data

US 2005/0070902 A1    Mar. 31, 2005

(51) Int. Cl.
*A61B 17/58* (2006.01)

(52) U.S. Cl. ........................................... 606/69; 606/64

(58) Field of Classification Search ................ 606/60, 606/62, 64, 67, 69, 71, 72, 73
See application file for complete search history.

(56) References Cited

U.S. PATENT DOCUMENTS

| 3,763,855 | A | * | 10/1973 | McAtee | 606/64 |
| 4,438,762 | A | * | 3/1984 | Kyle | 606/65 |
| 6,033,407 | A | * | 3/2000 | Behrens | 606/62 |
| 6,527,775 | B1 | * | 3/2003 | Warburton | 606/62 |

\* cited by examiner

*Primary Examiner*—David O Reip
(74) *Attorney, Agent, or Firm*—Ladas and Parry LLP

(57) ABSTRACT

An implant for fracture fixation having external portion shaped to be externally engaged on and secured to a stable bone fragment on one side of a bone fracture and an integral internal portion sized and shaped for being inserted into and accommodated in an intramedullary canal of an unstable bone fragment on an opposite side of the fracture. The internal portion has an end with a rounded tip of bullet-shape for fitting in an apical space at an endosteal surface of the unstable bone fragment to provide a bearing support for the unstable bone fragment over a large area.

59 Claims, 7 Drawing Sheets

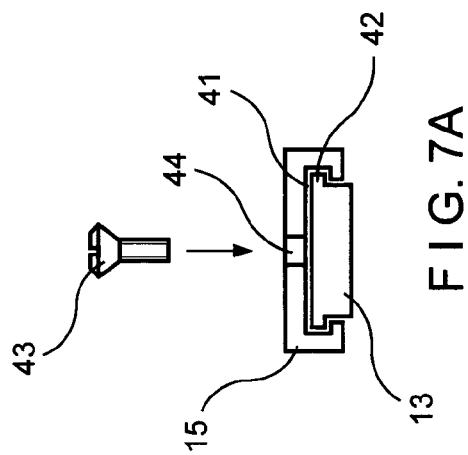
FIG. 7A
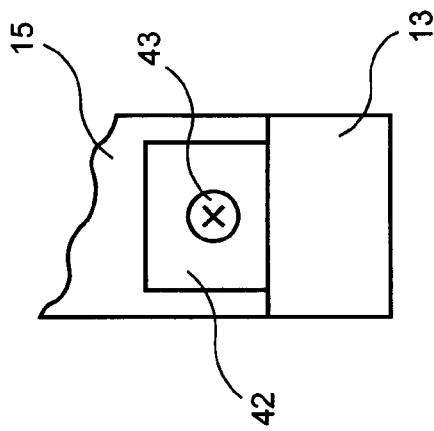
FIG. 7B
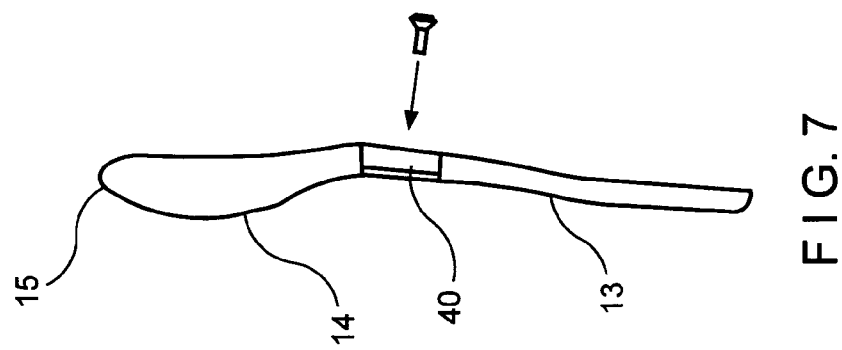
FIG. 7
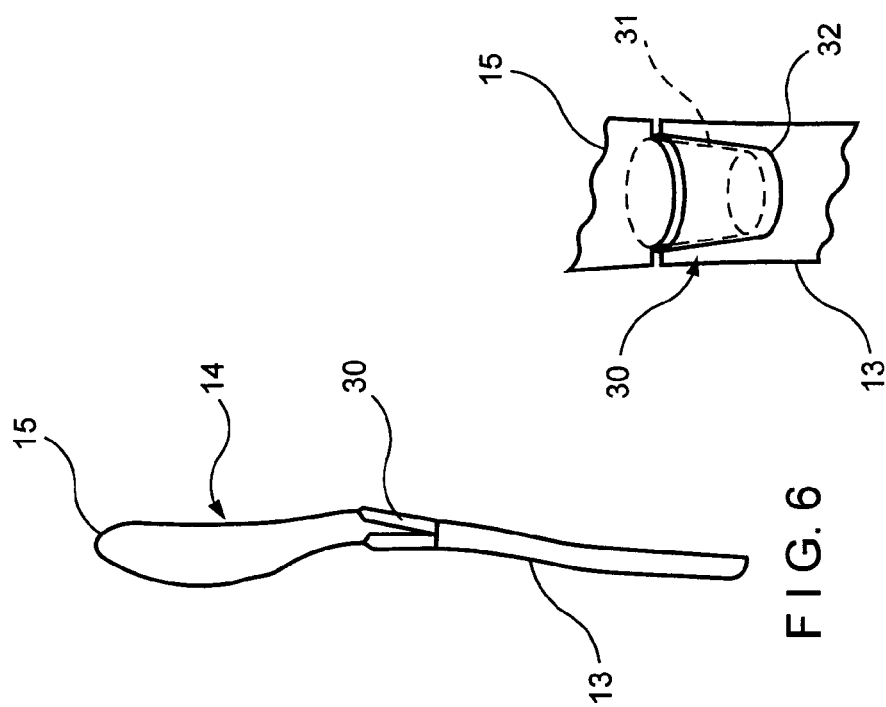
FIG. 6A
FIG. 6

INTRAMEDULLARY IMPLANT FOR FRACTURE FIXATION

FIELD OF THE INVENTION

The invention relates to fracture fixation devices and particularly to devices for fixation of distal fractures of the radius.

In particular, the invention relates to an intramedullary implant for such fracture fixation in which the implant includes a first portion adapted to be secured externally on stable bone and a second portion which enters into the intramedullary canal of the unstable bone fragment to be set and wherein the tip end of the second portion is shaped to fit in a space in an endosteal surface of the unstable bone fragment and suspend the unstable bone fragment by said tip end to prevent axial collapse or shortening of the unstable bone fragment.

In the case of the fracture of the distal radius, the invention provides that the tip end of the intramedullary implant engage the subchondral bone of the radial styloid to maintain its length and position.

The invention further relates to a method for fracture fixation with an intramedullary implant.

BACKGROUND

Fractures of bones in the body often require internal fixation to obtain satisfactory position of the fractured elements for healing. As a general rule, compression of the fractured ends is desirable for promoting fracture healing. Many internal fixation devices are based on this philosophy to promote compression of the fractured elements.

Some situations occur, however, where it is more important to maintain one fragment in a specific position in space in order to preserve proper function of the extremity. In some fractures, this means holding the fracture element out to length and preventing shortening. In other situations, this means preventing a fracture element from rotating into an abnormal angular position.

One example of this type of situation occurs in the context of a distal radius fracture that has a radial styloid or radial column fragment. If the radial styloid is not held out to length, the bones of the carpus (wrist) will subside proximally and result in high deforming loads across the fractured articular surface. This can lead to loss of reduction of the joint surface and malposition of the wrist. In addition, since the adjacent ulna is of normal length and the radius becomes short, significant dysfunction can occur to the adjacent radioulnar joint. Finally, translation of the radial styloid to the radial side causes the end of the articular surface to spread apart, resulting in incongruity of the articular surface and a poor clinical result.

Since it is extremely important to maintain radial length, fixation of distal radius fractures should prevent collapse of the radial column. In addition, it is desirable to prevent radial translation of the radial side of the wrist by providing a buttress to the radial column.

Current implants do not adequately address this problem of maintaining length to the radial styloid. A conventional radial pin plate requires the implant to be placed entirely on the surface of both fracture fragments and requires a larger exposure to apply the implant to the surface of the radial styloid. In addition, since the pins that cross the radial styloid are thin, the fragment can slide along the pins and lose length.

Standard buttress fixation plates placed either dorsally or volarly also do not adequately address this problem. These also require exposure of the entire surface of the bone, which can be detrimental because of stripping of the blood supply and irritation of the soft tissues. This type of approach requires a bulky plate to be placed on the superficial surface of the distal fragment in a region where many tendons and ligaments are in close apposition to the bone; this can result in tendon irritation and even rupture. In addition, because these plates are placed on the dorsal or volar surface, the only means available for supporting the distal articular surface is limited to cylindrical posts or screws that are placed through holes in the plate. Although the screws or posts may be locked into the plate to prevent angulation in relation to the hole in the plate, they can only cross transversely across the distal bone fragment to exit along the opposite cortex, either dorsally or volarly depending on the placement of the plate or tines that extend perpendicularly to the plate. As such they can only act to buttress the subchondral bone at the apex of concavity of the articular surface at a single point. In addition, this buttress effect occurs only along the side of the screw or post. Since these posts or screws are designed to cross the bone either from dorsal to volar or from volar to dorsal, it is not geometrically possible to angle the tip of a post or screw into the apical corner of the radial styloid using a dorsal or volar plate.

Fixation screws or posts through volar, dorsal, or even a radial sided plate can only buttress a fragment by contact between the fragment and the side of the screw or post. If this occurs, the screw or post is placed under torque, increasing the forces in both the implant and bone/implant interface. This torque may lead to loosening and make the bone fragment more prone to slip off the fixation post. Increased stresses in the bone implant interface also increase the risk of failure.

Finally, because of the complex geometry and intimate apposition of tendons and ligaments against the volar and dorsal surfaces of the radius, trying to secure a distal radial styloid fragment using dorsal or volar fixation is prone to complications and is generally not used.

Standard hip plates also provide a similar situation in which the plate is fixed distally with an external side plate and screws, and has a second part that is placed internally within the femoral head to secure this fragment. However, these implants are intentionally designed to allow sliding and impaction of the femoral head to promote union; in this circumstance the loss of length is a minor problem compared to the possibility of non-union by maintaining length. In addition, with the existing hip screws and blade plates, no mechanism is present to buttress the subchondral bone of the femoral head with a smooth tip. These devices gain fixation to the metaphyseal bone only with threads (hip screws) or a blade (hip nails).

SUMMARY OF THE INVENTION

An object of the present invention is to provide an implant adapted to overcome the limitations noted above by placing a large surface area of contact at the tip of a buttressing element against an apical corner of a subarticular fragment, such as the radial styloid. The tip of the buttressing element of the implant is configured with a blunt shape to supports the surface geometry of the subchondral bone of a fracture element from inside the osseous structure of the bone fragment. This loads the implant axially, and eliminates torque between the bone and implant, reducing the risk of failure. In addition, since the bone is suspended from the tip of the implant, like a tent being held by a tent post, fragment length is maintained.

In one embodiment, the end of the buttressing element is in the form of a smooth rounded tip of bullet-like shape in order to fit inside the radial styloid and prevent loss of length. The tip of the buttressing element is impacted against the endosteal side of the apical contour of the end of the radial styloid in order to hold it out to length; proximally, the buttressing element exits the bone and is fixed with screws to the radial shaft to secure it into position. The shape of the tip may be symmetrical or asymmetrical depending on the configuration of the apical contour.

Additional features of the invention provide improved insertion technique as well as the quality of fixation. One embodiment simplifies insertion by adding a cannulated track through the length of the implant to allow the implant to be placed over a guide wire. In another embodiment straight or angled crossing holes are formed in the implant in order to allow screws, posts or pins to be placed as locking fasteners across the tip of the implant from outside the bone, penetrating the implant like the locking screws on an interlocking nail. In further modifications of this latter embodiment, the crossing holes are threaded so that a crossing post can be inserted from outside the bone using an insertion guide that is attached to the proximal end of the implant. The crossing post is threaded and has a head secured on a washer. As it is locked across the tip of the implant within the radial styloid, an additional buttress radially is provided, preventing displacement of the radial column radially and preventing widening of the articular surface.

According to additional features the crossing fasteners can be angled from the tip of the radial styloid to further add fixation of this component by locking it to the implant therewithin. In addition, the crossing fasteners can be directed transversely across the radius to support the dorsal rim, volar rim and/or subchondral bone of the articular surface of the lunate facet from the implant. In this context, the implant not only secures the radial styloid out to length, but can be used as a base of support for other portions of the distal radius.

The buttressing element can be fashioned as a single, elongated implant having a base that is adapted to sit on the surface of the proximal fragment externally and be fixed thereto with standard bone screws. It also can be made as an implant having two major parts comprising a proximal external plate slidably secured to an internal buttressing element. Alternatively, the two parts may be coupled by a connecting hole (like a post on a volar buttress plate or a screw in a hip compression plate) or the buttressing element can be simply secured to the external part by machine screws.

According to a feature of the invention, the buttressing element can be connected to the external part by an adjustment mechanism to fix the buttressing element at a certain length from its attachment to the external part. This can be achieved, for example, either through an adjustment screw or simply providing a slotted bone screw hole in the external part to allow displacement of the buttressing element proximally or distally before it is secured proximally.

The buttressing element can be coupled to a dorsal or volar plate, using an angled base that redirects the connection to the volar or dorsal side, yet still providing an implant that achieves a buttress effect at the tip of the buttressing element.

According to one aspect of the invention, the implant serves for fixation of a fracture of the radius and comprises an elongated implant having a proximal portion adapted for connection to stable bone and a distal portion adapted for buttressing the radial styloid of an unstable bone fragment of the fracture. The distal portion is shaped for insertion into an intramedullary canal of the unstable bone fragment to enter the radial styloid and provide a broad buttress support for a tip end of the radial styloid at the endosteal surface thereof.

In a preferred embodiment, the end of the distal portion is of rounded bullet-like shape to fit within the apical corner at the tip end of the radial styloid.

In another aspect of the invention, the implant is not limited to fixation of fractures of the radius, but is more generally adapted to fixation of a fracture of any bone having one fragment with an end in the form of a conical surface, such as the distal end of the fibula, the medial malleolus of the ankle and the distal end of the ulna. Also, the buttressing part of the implant can be placed proximally and the end secured to the stable bone can be the distal end of the implant.

According to this aspect of the invention, the implant comprises a first part for fixation to a surface of a first bone fragment, and a second part for insertion within a second bone fragment, the second part having a tip end adapted to provide a broad abutment surface against an endosteal surface at a conical end of the second fragment to maintain length of the second bone fragment relative to the first for preventing axial collapse or shortening of the second bone fragment. The second or buttressing part can be located distally or proximally depending on the location of the fragment with the conical end.

According to a further aspect of the invention, a method is provided for fixation of distal and proximal fragments of a bone fracture comprising the steps of providing first and second integral parts of an implant for fracture fixation of the fragment, said first and second parts being adapted for engaging proximal and distal fragments of the bone, inserting one of said parts of the implant into an intramedullary canal of one of said bone fragments, such that an end of said one of the posts engages in an apical space at an endosteal surface of the one of said bone fragments, providing a blunt, rounded shape at said end of said one of the parts for broadly buttressing the one of said bone fragments at the apical space at the endosteal surface and fixing the other of said parts of the implant to the other of the bone fragments.

BRIEF DESCRIPTION OF THE DRAWINGS

FIG. 6 is a side view showing a first embodiment of a connection between distal and proximal portions of the implant.

FIG. 6A illustrates, on enlarged scale, the first embodiment of the connection between the distal and proximal portions of the implant.

FIGS. 7, 7A and 7B diagrammatically illustrate another embodiment of the connection between the distal and proximal portions of the implant.

DETAILED DESCRIPTION OF THE INVENTION

The invention will be described hereafter with reference to fixation of a fracture of the radius of the wrist utilizing an intramedullary implant which is braced against the apex of the lower tip of the radial styloid to serve as a prop or buttressing means to hold an unstable fragment of the fracture at length to prevent shortening. However, as will be evident to those skilled in the art, the invention is applicable to other fractures as well, in which the implant can be inserted into an intramedullary canal and braced in an inner apical surface of a bone fragment adjoining the fracture. Suitable examples are the distal end of the fibula, the medial malleolus of the ankle and the distal end of the ulna.

Figure 1:
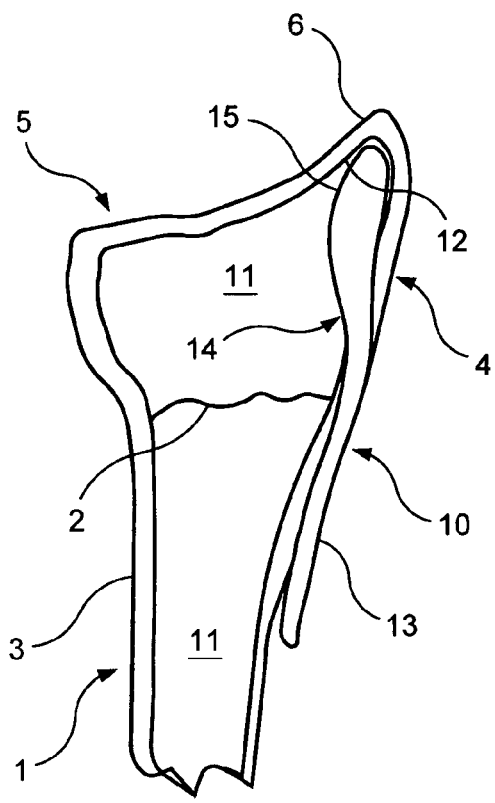
FIG. 1 is a diagrammatic, sectional view showing an intramedullary implant according to the invention installed at a fracture site in a bone.

Referring to FIG. 1, therein is seen a bone 1, namely the radius of the wrist, in which a fracture 2 is present at its distal end and forms a stable proximal bone fragment 3 and an unstable distal bone fragment 4. The distal bone fragment 4 has a distal end 5 which includes the radial styloid 6. Although the fracture 2 is illustrated in proximity to the distal end 5, the fracture can also be displaced proximally without altering the inventive concept.

The invention is based on utilizing an implant 10 which enters into the intramedullary canal 11 of the bone to engage an endosteal apical surface 12 at a corner at the tip of the radial styloid 6 to engage and brace the radial styloid and suspend it in a fixed position to prevent shortening or collapse of the radial styloid. In this regard, the implant 10 is axially loaded to prevent shortening of the unstable bone fragment 4. In addition to axially suspending the unstable bone fragment 4 out to length, the implant also can oppose lateral drift and rotation of the radial styloid.

The implant 10 has a proximal portion 13 and a distal portion 14. The proximal portion is disposed outside the bone and is engaged on and secured to the proximal, stable bone fragment 3 (as will be explained in more detail later). The distal portion 14 is sized and shaped for entry into the intramedullary canal 11 and it has a distal end or tip 15 of particular shape to be fitted into the space defined by the endosteal apical surface 12 for bearing against the subchondral part of the radial styloid of the unstable bone fragment 4 from therewithin, to buttress the unstable bone fragment over a large surface area thereof.

Figure 2:
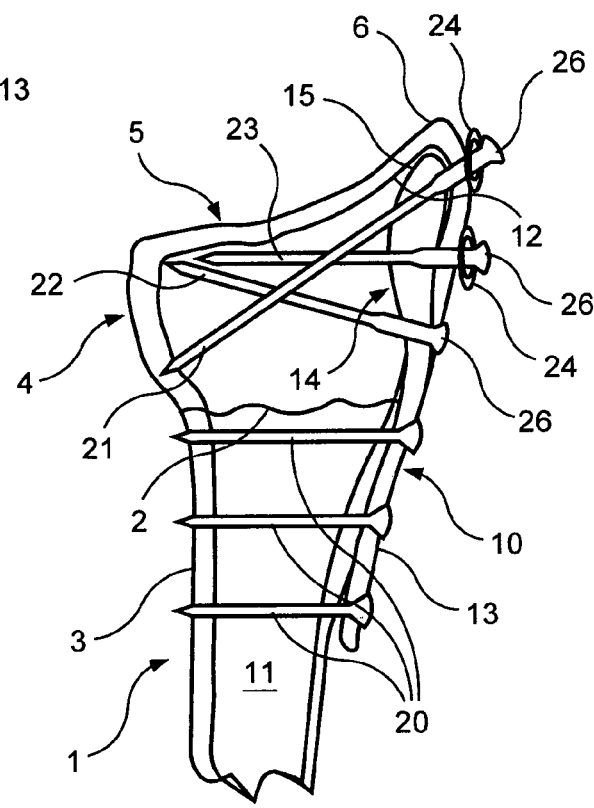
FIG. 2 is similar to FIG. 1 and illustrates means for securing the implant to the bone fragments of the fracture.
Figure 3:
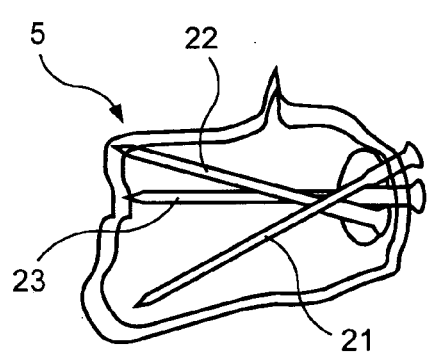
FIG. 3 is an end view looking distally into the radial styloid of the bone fragment.

Specifically, with reference to FIGS. 1 and 2, the tip 15 of the distal portion 14 of the implant 10 is tapered and rounded in a bullet-like shape to provide substantial congruency with the shape of the endosteal apical surface 12 at the subchondral bone at the apical corner of the radial styloid. The distal portion 14 widens and becomes thicker at it extends from the proximal portion 13 and it has a rounded cross-section which is oval as seen in FIG. 3. The tip 15 has an enlarged or blunt end as compared to conventional buttress plates or wires to provide a large bearing area against the bone to prevent penetration and perforation through the subchondral bone of the distal fragment. The tip end can be symmetrical or asymmetrical for conforming to the shape of the apical corner of the subchondral bone.

Figure 4:
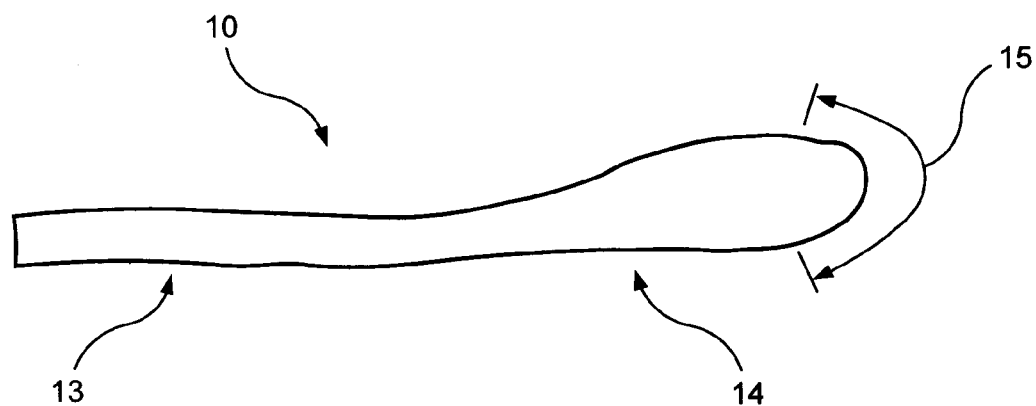
FIG. 4 is a top view of the implant.
Figure 5:
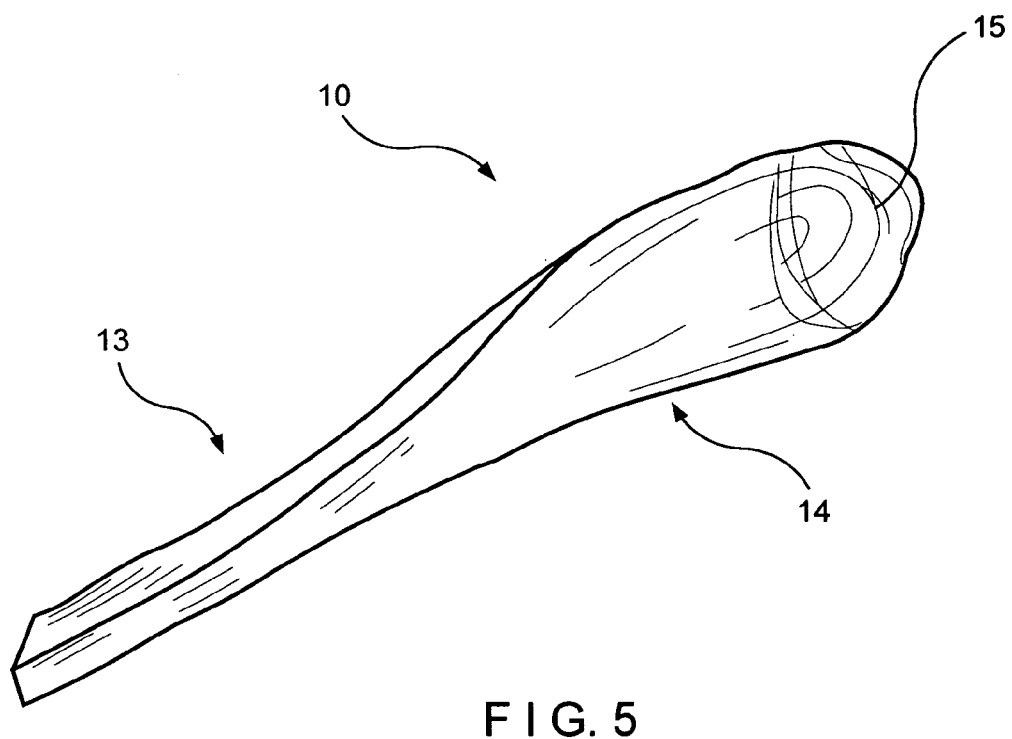
FIG. 5 is a perspective view of the implant.

As shown in FIGS. 4 and 5 the implant 10 has a slender, elongated shape; the proximal portion 13 has an approximate rectangular cross-section and it can be flat or slightly curved in order to be mounted on and secured to the outer surface of the proximal stable bone fragment, usually the shaft of the radius. This is the external part of the implant which extends at the outer surface of the bone. The proximal portion 13 merges into the distal portion 14 which extends into the intramedullary canal 11. The distal portion 14 becomes wider and thicker than the proximal portion and its cross-section becomes rounded and can have an oval shape. In the illustrated embodiment, the distal portion 14 is offset from the proximal portion 13 and its oval shape enables it to pass through the intramedullary canal and lie against the inner surface of the cortex. The tip 15 is shaped to enter the space defined by the apical space 12 and provide a broad support function over a large area. For this purpose, the tip 15 has a rounded, tapered shape of bullet-like form. In the particular embodiment, the tip 15 has a parabolic, ogival contour adapted to provide congruency with the endosteal apical surface 12 to enable the implant to hold the distal fragment at length and prevent shortening or collapse thereof while also providing restraint against lateral and rotational movement of the distal fragment.

FIG. 2 shows an installed state of the implant 10 for fixation of fracture 2. Therein, it is seen that the proximal portion 13 of the implant 10 is fixed to the stable, proximal fragment 3 by bone fixation screws 20. It may be sufficient for the distal portion 14 to be secured by fitting the tip 15 in the apical space but additional securing of the distal portion 14 to the radial styloid 6 can be achieved by using transstyloid crossing fasteners 21, 22 and 23. The crossing fasteners can be in the form of pins, wires, rods, pegs or screws. The crossing fasteners can be smooth over their entire length or they can have threaded portions at their ends for threadably engaging the distal portion 14 and/or they can have threaded portions at or near their advancing ends for threadably engaging the bone. The choice of the particular crossing fasteners is made by the surgeon depending on the circumstances of the particular case, such as patient age, bone fragility, geometry of the radial styloid, etc.

Hereafter, the crossing fasteners will be described as conventional pegs, which are widely used for fixation purposes, but this is in not limiting as to the particular fasteners as explained above.

The crossing pegs 21, 22 and 23 are disposed in different planes at different angles to lock the distal portion 14 in place and prevent relative movement between the distal portion 14 and the distal fragment 4. In this regard, the peg 23 may be inclined volarly and the peg 22 inclined dorsally. The pegs may be provided with washers 24, such as shown with pegs 21 and 23 in FIG. 2 which are seated under heads 26, to prevent over compression of the bone by the heads 26 on the pegs while other pegs, such as peg 22, may be inserted flush with the surface of the implant 14. Two or more washers may be integrated into a single common plate in order to engage the heads of more than one fastener with a single washer.

Figure 9A:
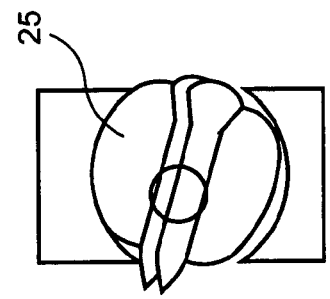
FIG. 9 is a sectional view, similar to FIG. 2, and shows a modified installation of one of the crossing fasteners in the implant.
Figure 9:
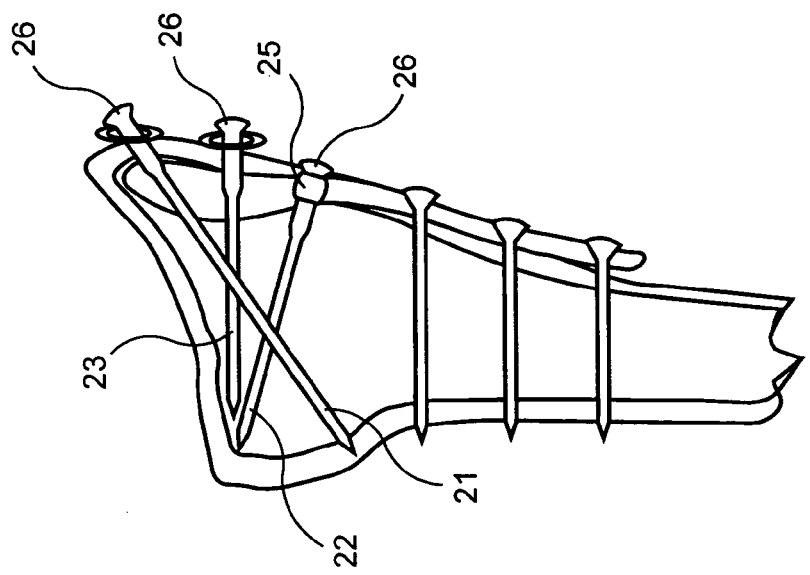

In a particular embodiment, as illustrated in FIGS. 9 and 9A, the peg 22, is engaged in the bone via a bearing 25 which is provided with longitudinal slits around its periphery so as to be expandable when the peg is inserted into a hole in the bearing. The bearing has a generally spherical outer surface which matches with an inner spherical surface of a hole, in the bone in which the bearing is seated. The peg 22 can be partially inserted into the bone and the angular position of the peg can be adjusted by rotation of the bearing in the bone to finalize the position of the radial styloid when setting the fracture. The peg 22 has a tapered thread in proximity to the head 26 thereon so that when the peg 22 is fully inserted into the bearing, the bearing 25 is expanded and is locked in the hole in the bone. The bearing may have a tab extending from its surface that engages a slot in the hole in the end of the implant to prevent rotation of the bearing as the peg is advanced, and/or limit a range of insertion angles of the peg to a predefined range. Although in this example peg 22 is illustrated with a lockable bearing assembly, to those skilled in the art it is apparent that this assembly could be used with any fasteners of the device The implant 10 can be made as a one-piece integral body of a light weight, strong metal, such as, titanium or stainless steel. It can also be made in two parts to enable longitudinal, translational, or rotational adjustment of the proximal and distal portions of the implant or it can be made as an independent modular assembly of different lengths of the proximal and distal portions in order to reduce inventory. The implant can be made in two parts which are rotatably adjustable to enable the implant to be fixed to the dorsal or volar surface of the bone.

FIGS. 6 and 6A show one embodiment of an adjustable connection 30 between the proximal portion 13 and the distal portion 14. The connection 30 is in the form of a Morse taper which includes a conical portion 31 on one of the portions (here the distal portion 14) and a conical recess 32 on the proximal portion 13. The arrangement can be reversed and the conical portion can be placed on the proximal portion and the recess on the distal portion. The angles of conicity of the portions 31 and 21 differ by a small amount, for example, 2 to 3 degrees, whereby the distal and the proximal portions can be tightly engaged at adjusted axial or angular positions by axially forcing conical portion 31 into conical recess 32. In a variation (not shown), ridges and corresponding valleys can be provided on the tapered surfaces to limit the torsional position of the proximal and distal portions to a set of predetermined rotational positions.

In another embodiment as shown in FIGS. 7, 7A and 7B, a tongue in groove connection 40 is provided between the opposed ends of the proximal and distal portions 13 and 14. In this embodiment, a groove 41 is provided in one of the portions of the implant (in this case distal portion 14) and a tongue 42 is provided on the proximal portion 13. The tongue 42 is slidable in the groove 41 and is secured in an axially adjusted position by a machine screw 43, which can be inserted in one of a plurality of holes 44 or in a slotted hole.

Figure 8:
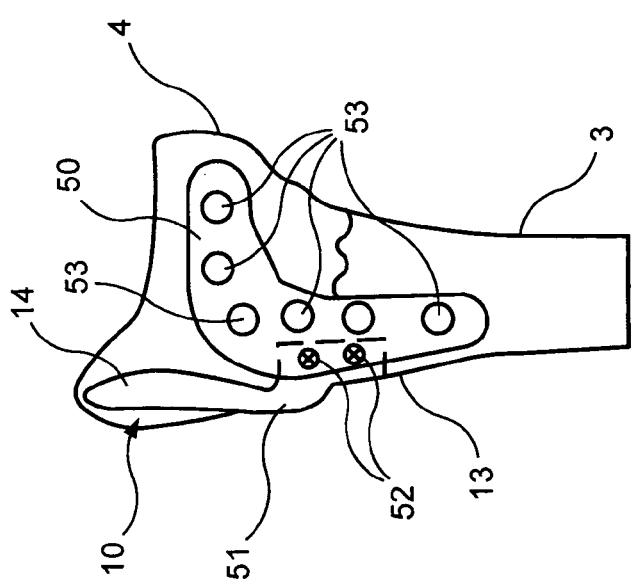
FIG. 8 illustrates another embodiment of the installation of the implant.

Referring next to FIG. 8, therein is shown a two part connection in which the proximal portion 13 of the implant 10 is secured to the bone through a connecting plate 50. The connecting plate 50 is disposed on the volar surface of the bone and fixed to the bone, and the distal portion 14 enters the intramedullary canal from the lateral (or radial) side of the bone, where the bone flairs out wider at 51. The connecting plate 50 is of L-shape and wraps around the volar surface of the radius to join the two bone fragments 3, 4 together. The plate 50 is secured to the implant by connecting screws 52 and the plate has holes 53 for bone screws (not shown) for securing the plate to the bone fragments.

The installation of the implant is carried out as shown in FIGS. 10–17.

Figure 10:
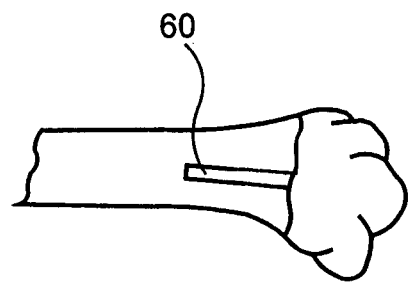
FIGS. 10–17 show successive stages in the installation of the fracture fixation device.

Referring to FIG. 10, a slot 60 is produced along the mid-radial line of the radial shaft of the radius just proximal to the fracture 2. The slot allows seating of the proximal portion 13 of the implant and avoids radial translation of the distal fragment. Typically, the slot is approximately 4 to 5 mm wide and 1 cm in length, and the slot deepens toward the fracture site. The slot 60 may be prepared with either a high speed burr, or other suitable instrument.

Figure 11:
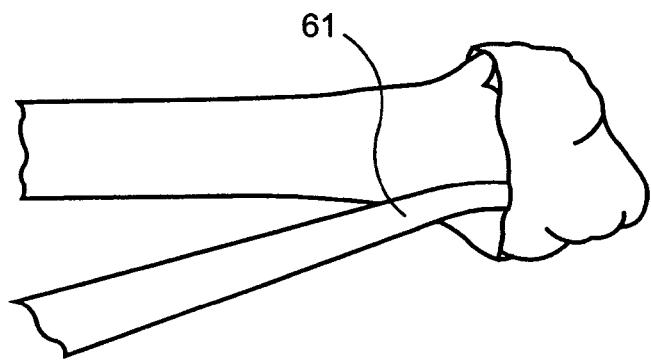

FIG. 11 shows an awl 61 inserted along the subcortical bone of the radial styloid to the tip of the radial styloid. The position of the tip is confirmed on an image intensifier (not shown) and a determination is made of the proper length implant to be used. The awl may be cannulated so as to be placed over a guide wire to ensure proper orientation.

Figure 12:
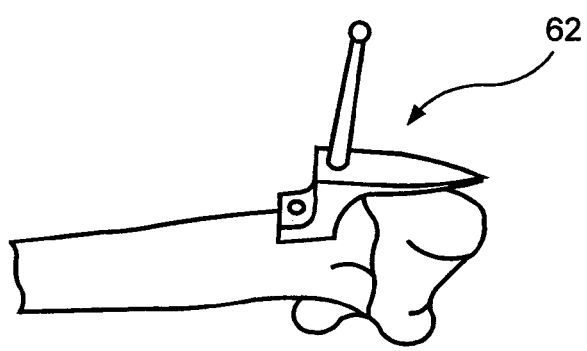

FIG. 12 shows an alignment jig 62 attached to the implant and the implant is inserted into the prepared intramedullary canal in the radial styloid of the unstable fragment. The position of the proximal portion 13 of the implant is aligned so that a referencing arm of the alignment jig is dorsal to the tendons of the first dorsal compartment, and the pointer is aimed at the distal tip.

Figure 13:
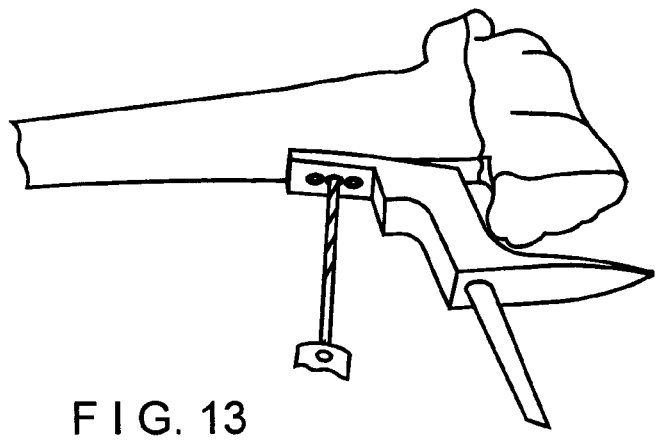

As shown in FIG. 13 a hole is then drilled in the proximal cortex and tapped and a bone screw is inserted into a slotted hole at the proximal portion of the implant. The screw is positioned in a central location of the slotted hole to allow fine adjustment of the position of the implant.

Figure 14:
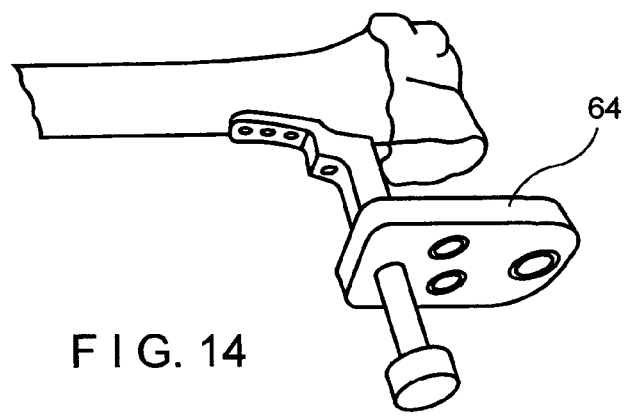

A distal targeting device 64 is firmly attached to the radial styloid as shown in FIG. 14 to allow placement of the interlocking transstyloid pegs.

Figure 15:
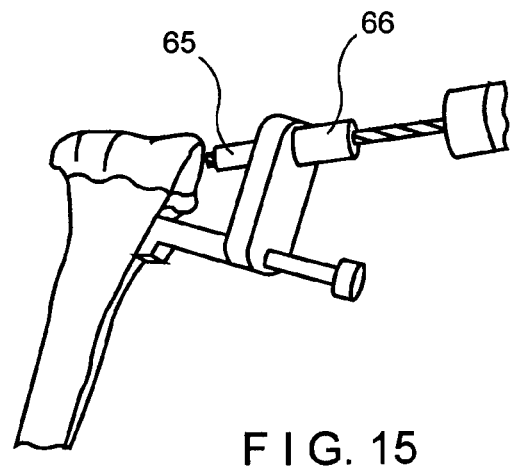

An outer targeting sleeve 65 and drill guide 66 are assembled on the distal targeting device, as shown in FIG. 15, and a hole is drilled for placement of a peg. An image intensifier is used to confirm the appropriate position prior to placement of the peg.

Figure 16:
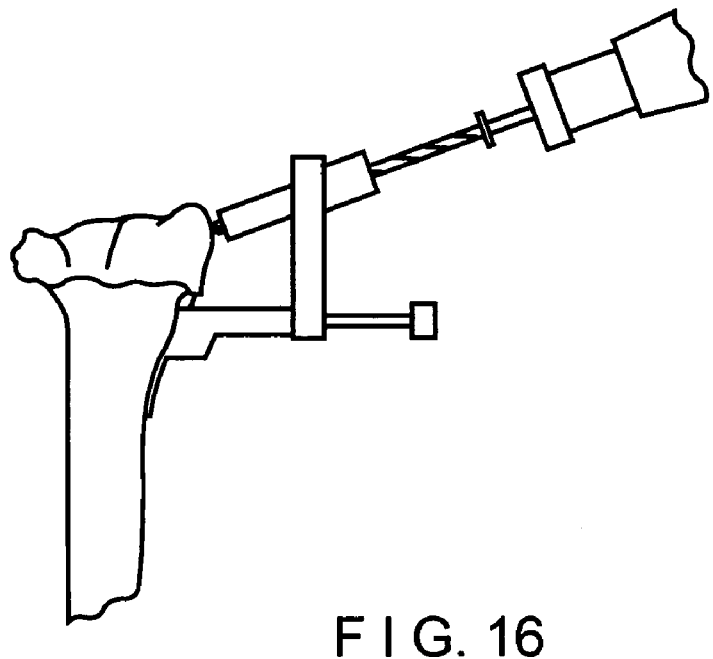

As shown in FIG. 16, an appropriate length peg and washer is inserted through the outer sleeve. The end of the peg is threaded to screw into the threaded hole in the implant. Care is taken to position the peg to avoid contact with the tendons. The proximal holes for the pegs may be used with a washer to provide a buttress to the radial column, or the peg may be used without a washer and locked directly into the implant.

Figure 17:
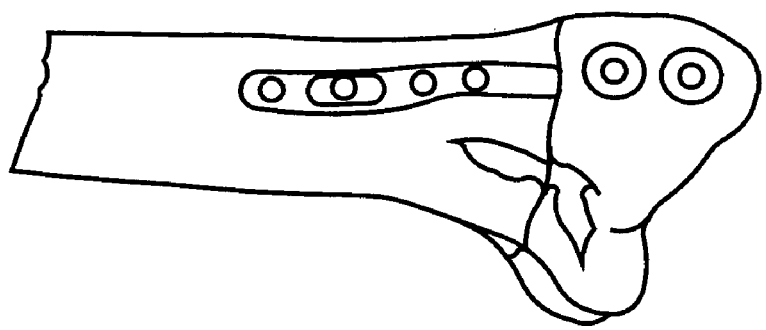

Additional interlocking transstyloid pegs and bone screws are applied as needed as shown in FIG. 17. For comminuted fractures, additional supplemental fixations with other elements are used as necessary.

In one variation of the peg design, the machine thread on the peg stops 1–2 mm short of the head of the peg. This allows insertion of the peg with a washer but prevents excessive compression from causing the washer to crack through the bone. Pegs may be designed to have either a smooth or threaded surface along the leading shaft portion of the peg (not shown).

Although the invention has been described in relation to particularly embodiments thereof, it would become apparent to those skilled in the art that numerous modifications and variations can be made without departing from the scope and spirit of the invention as defined in the attached claims.

What is claimed is:

1. A fracture fixation system for fixation of a first bone fragment and a second bone fragment of a bone fracture, said fixation system comprising a buttressing element having a first part for fixation to a surface of a first bone fragment, and a second part for insertion within an intramedullary canal of the second bone fragment, said second part having a tip end shaped with a broad contact surface serving as a means for abutment against an endosteal surface at an end of the second bone fragment for maintaining length of the second bone fragment relative to the first bone fragment for preventing axial collapse or shortening of the second bone fragment, and a plurality of crossing fasteners for securing said second part to said second bone fragment, two or more of said crossing fasteners being positioned along different planes.

2. The fracture fixation system of claim 1, wherein said tip end of said second part is shaped to also maintain transverse and angular position of the second bone fragment.

3. The fracture fixation system of claim 1, comprising bone screws for securing said first part to the first bone fragment.

4. The fracture fixation system of claim 1, wherein said first and second parts form a continuous implant.

5. The fracture fixation system of claim 1, wherein said second part is connected to said first part by a screw engaged in a threaded hole.

6. The fracture fixation system of claim 1, wherein said second part is connected to said first part by a slidable connection and is secured by a screw that threads into said second part.

7. The fracture fixation system of claim 1, wherein said second part is connected to said first part by a morse taper.

8. The fracture fixation system of claim 1, wherein said first and second parts are joined by a tongue and groove connection.

9. The fracture fixation system of claim 8, wherein said tongue and groove connection is secured by a screw.

10. The fracture fixation system of claim 1, wherein said second part has a blunt end to prevent penetration and perforation through a subchondral bone of the second fragment.

11. The fracture fixation system of claim 1, wherein said tip end of the second part is symmetrical or asymmetrical for conforming to a shape of an apical corner of a subchondral bone at said endosteal surface.

12. The fracture fixation system of claim 1, in which a first said crossing fastener is directed dorsally, a second is directed volarly and a third is inclined toward said first part.

13. The fracture fixation system of claim 1, wherein the bone fracture is of the radius, and said tip end of said second part is contoured with an ogival or bullet shape for conforming to a pointed, apical geometry of a subchondral bone inside a tip of a radial styloid of the second bone fragment.

14. The fracture fixation system of claim 1, comprising a washer engaged beneath a head of at least one of said crossing fasteners.

15. The fracture fixation system of claim 14, wherein said second portion has a blunt shaped end.

16. The fracture fixation system of claim 15, wherein said blunt shaped end is of rounded bullet-like shape.

17. A fracture fixation system for fixation of a first bone fragment and a second bone fragment of a bone fracture, said fixation system comprising a buttressing element having a first part for fixation to a surface of a first bone fragment, and a second part for insertion within an intramedullary canal of the second bone fragment, said second part having a tip end shaped with a broad contact surface serving as a means for abutment against an endosteal surface at an end of the second bone fragment for maintaining length of the second bone fragment relative to the first bone fragment for preventing axial collapse or shortening of the second bone fragment, wherein the bone fracture is of the radius, and said second part has internal crossing holes to allow passage of crossing fasteners for securing the second part to the second bone fragment.

18. The fracture fixation system of claim 17, wherein said crossing holes are relatively angulated with respect to one another to receive a range of insertion angles of said crossing fasteners.

19. The fracture fixation system of claim 18, comprising an external guiding arm attachable to said first part, to guide placement of the crossing fasteners in the crossing holes.

20. The fracture fixation system of claim 19, in which the crossing holes position the crossing fasteners at different angles relative to each other.

21. The fracture fixation system of claim 17, wherein said crossing fasteners have heads for compressing external bone of said distal fragment against said second part.

22. The fracture fixation system of claim 21, comprising washers beneath the heads of the fasteners.

23. The fracture fixation system of claim 17, wherein said second part is secured in extension with said first part.

24. The fracture fixation system of claim 17, wherein said first part is torsionally rotatable with respect to said second part for selectively fixing the first part to a volar or dorsal surface of the bone.

25. The fracture fixation system of claim 17, wherein said first portion includes a flat part adapted for connection on the stable bone fragment.

26. An intramedullary buttressing member comprising an elongated element including a first portion of flattened shape adapted for mounting on a bone fragment on one side of a bone fracture and a second portion smoothly merging with and extending from said first portion, said second portion having a rounded shape adapted for passage in an intramedullary canal in a bone fragment on an opposite side of the fracture, said second portion being formed with a tip end of rounded, bullet-like shape providing a broad buttressing surface.

27. The intramedullary buttressing member of claim 26, wherein said tip end of rounded, bullet-like shape is adapted for congruency with the shape of an endosteal surface at a tip of a radial styloid of said bone fragment on the opposite side of the fracture.

28. The intramedullary buttressing member of claim 26, wherein said first portion is adapted to be situated externally along a radial side of the bone fragment on said one side of the fracture.

29. The intramedullary buttressing member of claim 26, wherein said first portion is adapted to be situated along a volar or dorsal side of the bone fragment on said one side of the fracture.

30. The intramedullary buttressing member of claim 26, wherein said second portion is torsionally rotatable with respect to said first portion for selectively fixing the first portion to a volar or dorsal surface of the bone.

31. The intramedullary buttressing member of claim 26, wherein said first and second portions are separate parts joined together.

32. The intramedullary buttressing member of claim 31, wherein said first and second portions are joined together by at least one screw.

33. The intramedullary buttressing member of claim 31, wherein said first and second portions are joined by a tongue in groove connection.

34. The intramedullary buttressing member of claim 31, wherein said first and second portions are connected by a press fit.

35. The intramedullary buttressing member of claim 26, in combination with crossing fasteners adapted for passage through the radial styloid to engage said second portion crosswise.

36. The combination of claim 35, in which one of the crossing fasteners is angled dorsally or volarly.

37. The intramedullary buttressing member of claim 27, in which one of the crossing fasteners is angled with a proximal inclination.

38. The intramedullary buttressing member of claim 26, wherein said tip end of said second portion is shaped for supporting a radial styloid of the bone from within the intramedullary canal thereof and for buttressing the radial styloid axially of the second portion to maintain position and length of the second bone fragment.

39. The intramedullary buttressing member of claim 26, wherein said tip end of bullet-like shape has a configuration to enable said tip end to enter an apical space at an endosteal surface of the bone fragment on the opposite side of the bone fracture.

40. The intramedullary buttressing member of claim 39, wherein said second portion widens and increases in thickness as it extends from said first portion and provides a rounded elongated cross-section which smoothly merges with said tip end of bullet-like shape.

41. The intramedullary buttressing member of claim 40, wherein said first and second portions merge in a region at which the intramedullary buttressing member is adapted to pass through bone cortex so that said first portion is able to be mounted superficially on said bone fragment on said one side of the fracture while said second portion is able to enter the intramedullary canal of the bone fragment on the opposite side of the fracture.

42. A method for fixation of distal and proximal fragments of a fracture of the radius, said method comprising the steps of:
providing first and second integral parts of an implant for fracture fixation of the radius;
said first and second parts being adapted for respectively engaging proximal and distal fragments of the radius;
inserting the second part of the implant into an intramedullary canal of the distal fragment and into the radial styloid of the distal bone fragment;
providing a blunt shaped end on said second part for broadly engaging and buttressing an endosteal surface of the radial styloid; and
fixing the first part of the implant to the proximal bone fragment.

43. The method of claim 42, wherein said first and second parts of the implant are formed as one piece.

44. The method of claim 42, wherein said first and second parts of the implant are threadably secured.

45. The method of claim 42, comprising pressing the distal fragment against the tip of the second part and securing crossing fasteners into the distal fragment and said second part.

46. The method of claim 42, comprising inserting crosswise fasteners through the distal bone fragment into the second part of the implant in proximity to said blunt shaped end.

47. The method of claim 46, comprising applying compression force on the second bone fragment by said crosswise fasteners.

48. The method of claim 42, wherein said crosswise fasteners are inserted at different angles in said bone fragment and said second part of the implant.

49. The method of claim 42, comprising forming a groove in said proximal bone fragment in which said first part of the implant is secured.

50. The method of claim 42, wherein said blunt shaped end of said second part is formed with an ogival or bullet shape in conformance with an apical space at the endosteal surface of the subchondral bone inside the radial styloid, and wherein the second part applies axial pressure against said endosteal surface when the first part is secured to the proximal bone fragment.

51. Apparatus for fixation of distal and proximal fragments of a fracture of the radius, said apparatus comprising:
an implant having first and second integral parts for fracture fixation of the radius;
said first and second parts being adapted for respectively engaging proximal and distal fragments of the radius;
said second part being sized and shaped for being inserted into an intramedullary canal of the distal fragment and into the radial styloid of the distal fragment;
said second part having a rounded end of ogival or bullet shape in conformance with an apical space at the endosteal surface of the subchondral bone inside the radial styloid to fit and conform in said space for buttressing the endosteal surface of the radial styloid; and
fixation means for fixing said first part to the proximal bone fragment.

52. The apparatus of claim 51, wherein said first and second parts of the implant are formed as one piece.

53. The apparatus of claim 51, wherein said first and second parts of the implant are threadably secured together.

54. The apparatus of claim 51, comprising crossing fasteners secured in the distal fragment and said second part to hold the tip of the second part pressed against the distal fragment.

55. The apparatus of claim 51, comprising crosswise fasteners for passing through the distal bone fragment into the second part of the implant in proximity to said blunt shaped end.

56. The apparatus of claim 55, wherein said crosswise fasteners extend at different angles in said bone fragment and said second part of the implant.

57. The apparatus of claim 55, wherein said crosswise fasteners are angled for applying compression force on the distal bone fragment.

58. The apparatus of claim 55, wherein said rounded end of ogival or bullet shape is in conformance with an apical space at an endosteal surface of the subchondral bone inside the radial styloid to fit in said space, and the second part applies axial pressure against said endosteal surface when the first part is secured to the proximal bone fragment.

59. The apparatus of claim 51, wherein said first part has a lower surface shaped for being mounted externally on the proximal bone fragment such that the implant extends partly inside the intramedullary canal of the distal fragment and partly outside the bone on the proximal bone fragment.

* * * * *